(12) United States Patent
Wilson

(10) Patent No.: US 8,739,608 B2
(45) Date of Patent: Jun. 3, 2014

(54) INSTRUMENT FOR USE WITH FLUID

(75) Inventor: Allan Walter Wilson, Hamilton (NZ)

(73) Assignee: DEC International NZ Limited, Hamilton (NZ)

( * ) Notice: Subject to any disclaimer, the term of this patent is extended or adjusted under 35 U.S.C. 154(b) by 615 days.

(21) Appl. No.: 12/743,058

(22) PCT Filed: Nov. 14, 2008

(86) PCT No.: PCT/NZ2008/000310
§ 371 (c)(1),
(2), (4) Date: May 14, 2010

(87) PCT Pub. No.: WO2009/064205
PCT Pub. Date: May 22, 2009

(65) Prior Publication Data
US 2010/0246317 A1    Sep. 30, 2010

(30) Foreign Application Priority Data

Nov. 14, 2007 (NZ) .......................... 563464

(51) Int. Cl.
*G01N 11/12* (2006.01)
(52) U.S. Cl.
USPC .......... 73/54.18; 73/54.15; 366/142; 366/273
(58) Field of Classification Search
CPC ...... G01N 11/10; G01N 11/12; G01N 11/105
USPC ........... 73/51.18, 54.28, 54.15; 366/118, 142, 366/273
See application file for complete search history.

(56) References Cited

U.S. PATENT DOCUMENTS

| 2,034,658 | A |   | 3/1936  | Jones at al.              |
|-----------|---|---|---------|---------------------------|
| 2,491,389 | A | * | 12/1949 | Norcross ......... 73/54.18 |
| 2,630,819 | A | * | 3/1953  | Norcross ........... 137/92 |
| 3,512,396 | A | * | 5/1970  | Tsuneo ........... 73/54.21 |
| 3,686,931 | A | * | 8/1972  | Norcross ......... 73/54.16 |
| 3,734,119 | A |   | 5/1973  | Nudds                     |
| 4,175,425 | A | * | 11/1979 | Brookfield ........ 73/54.28 |
| 4,875,362 | A |   | 10/1989 | Skallen                   |
| 5,120,135 | A | * | 6/1992  | Ullman ........... 366/273 |
| 5,503,003 | A | * | 4/1996  | Brookfield ........ 73/54.32 |
| 5,798,454 | A |   | 8/1998  | Nakazeki et al.           |
| 5,959,196 | A | * | 9/1999  | Norcross, Jr. ...... 73/54.18 |
| 6,065,865 | A | * | 5/2000  | Eyraud et al. ...... 366/273 |
| 6,112,581 | A | * | 9/2000  | Scheider et al. ..... 73/54.24 |

(Continued)

FOREIGN PATENT DOCUMENTS

| GB | 1215347 | 12/1970 |
|----|---------|---------|
| JP | 1054332 | 3/1989  |

OTHER PUBLICATIONS

International Search Report, International Searching Authority, PCT/NZ2008/000310, dated May 6, 2009.

(Continued)

*Primary Examiner* — David Sorkin
*Assistant Examiner* — Abbas Rashid
(74) *Attorney, Agent, or Firm* — Greer, Burns & Crain, Ltd.

(57) ABSTRACT

An instrument for use with fluid which includes a mixing element, and a container to hold the fluid to be mixed, characterised in that the mixing element includes a sensor that assists to measure a parameter of fluid.

2 Claims, 9 Drawing Sheets

(56) References Cited

U.S. PATENT DOCUMENTS

| | | | |
|---|---|---|---|
| 6,663,276 B2* | 12/2003 | Yale | 366/192 |
| 2003/0192366 A1* | 10/2003 | Taylor | 73/54.32 |
| 2004/0165474 A1* | 8/2004 | Nesbitt et al. | 366/142 |
| 2005/0087002 A1* | 4/2005 | Kanzaki et al. | 73/54.28 |

OTHER PUBLICATIONS

International Preliminary Report on Patentability, International Searching Authority, PCT/NZ2008/000310, dated Feb. 18, 2010.

* cited by examiner

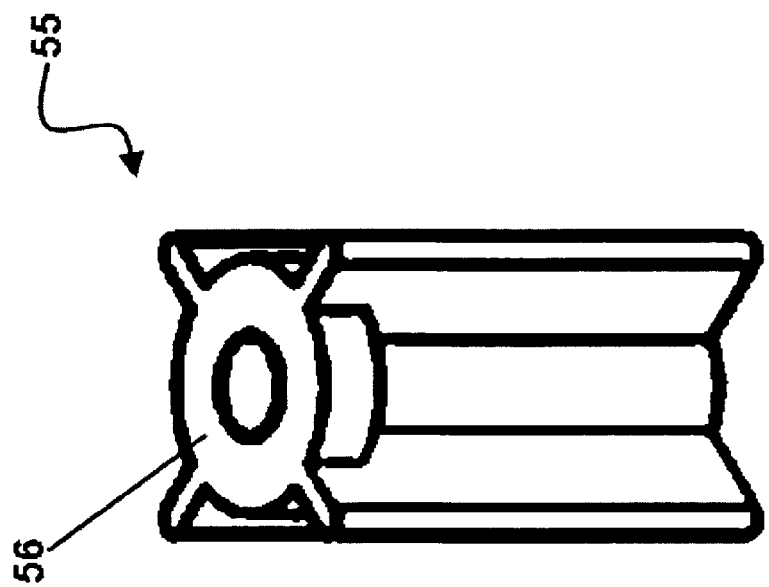
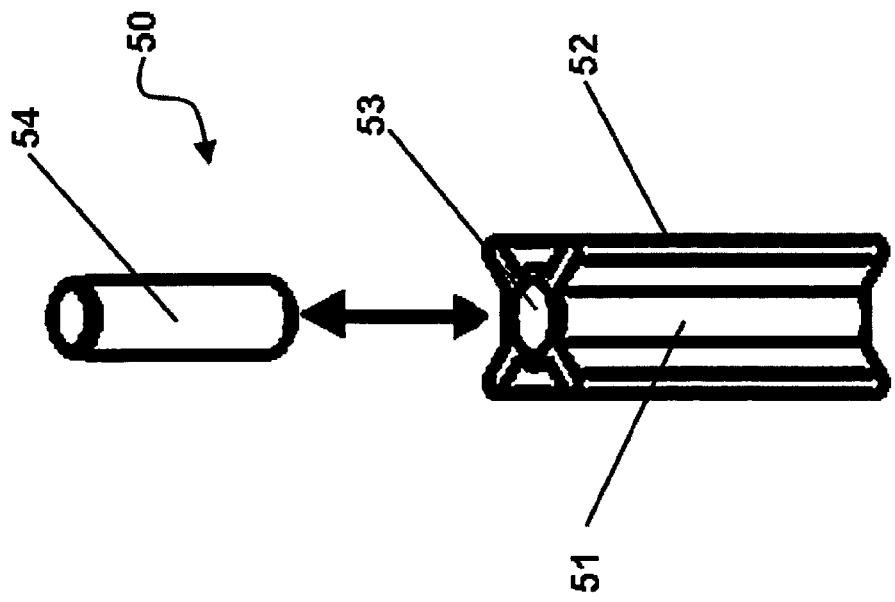

INSTRUMENT FOR USE WITH FLUID

STATEMENT OF CORRESPONDING APPLICATIONS AND PRIORITY

The present application is related to, claims the priority benefit of, and is a U.S. national stage application of, International Patent Application Serial No. PCT/NZ2008/000310, filed Nov. 14, 2008, which is related to, and claims the priority benefit of, New Zealand Patent Application Serial No. 563464, filed Nov. 14, 2007. The contents of each of these applications are hereby incorporated by reference in their entirety into this disclosure.

TECHNICAL FIELD

The present invention relates to an apparatus for use with fluid samples. The invention has particular application to the mixing and determining of viscosity of fluids.

BACKGROUND ART

For analysis of viscous substances it is desirable to have a homogenous, or close to homogenous, sample. This is to ensure that analysis of the substance is not affected by an inconsistent sample. To ensure consistency of a sample requires thorough mixing of the substance, which is usually a fluid.

There are a number of methods of mixing viscous fluids to ensure an adequately homogenous sample.

The most common method is the use of a motor driven single blade, or a plurality of blades, through the fluid. This can require a rather large machine which is not always suitable if the container in which the fluid is held is of a small size.

Careful control of the motor speed is also required, to ensure that the sample is not excessively agitated, as this may lead to foaming of the sample.

A stirrer which utilises a motor for its mixing drive can also be noisy. This is a disadvantage if the apparatus is intended for use in a laboratory situation.

Another disadvantage of a motorised stirrer is that they require lubrication on account of its various moving parts. This lubricating agent can contaminate the container or the fluid being analysed, a concern if precise data is required. This is also a concern if the fluid is to remain food grade quality.

Another method particularly favoured in science laboratories for mixing or stirring of fluids is the use of a magnetic stirrer. These are capsule like magnets which are placed into the container holding the fluid to be mixed. The container is then placed over an electromagnet which causes a rotating magnetic field, thus causing rotational movement of the stirrer and subsequent mixing of the fluid.

These magnetic stirrers are quieter and more efficient than motorised stirrers, but none the less some problems arise in their use for mixing.

Many items of science glassware are provided with inlets or outlets at their base or around the lower portion of the sidewalls of the container. These allow additional fluids or substances to flow into or out of the container as required. Traditional magnetic stirrers and stirring paddles can obstruct these orifices when in use.

Traditional magnetic stirrers are also only suitable for mixing fluids of a relatively low viscosity. Fluids of a high viscosity can be difficult to overcome for the magnetic field causing rotation of the stirrer, unless a particularly large magnet is used. A larger magnet also requires a larger electromagnet to cause the rotational magnetic field.

A variation on the use of magnetic forces for mixing and stirring fluids is the method and apparatus disclosed in New Zealand Patent No. 516057.

This invention uses a paddle configured in the lid of a container in which the fluid to be mixed is held. A solenoid causes a pulsing magnetic field, which in turn causes a reciprocating motion of the paddle and subsequent mixing of the fluid.

A disadvantage of the aforementioned patent is that it is also necessary, if a range of glassware of varying sizes is used in a laboratory, to have a stirring mechanism which is specific to each size container.

The use of this method of mixing requires the container to be closed when in use. This is not advantageous in some situations which require additional substances to be added to the fluid while it is being stirred.

The use of a closed top container can also make it difficult for an observer to determine visually if the fluid is sufficiently homogenized.

At present, there are no provisions in mixing apparatus to allow for accurate determination of some of the properties of mixed fluids. Usually a visual check is performed as the fluid is mixed.

Alternatively, at stages throughout the mixing process, mixing is halted and a measuring instrument is used to assess the mixed fluid, with mixing recommencing if measurements deem it necessary. This can be time consuming, particularly if the process needs to be repeated several times before an adequate homogenized sample is realised.

Alternatively, other instruments, such as temperature gauges and other fluid parameter measuring instruments can be used to assess the mixed fluid. However, these, such as vertical descent spheres to assess fluid density or viscosity, can often impede or block inlet or outlet ports into the container, and this can affect the quality of the assessment of the fluid.

All of these problems arise with regard to the specific task of trying to assess the somatic cell count (SCC) of milk.

A typical way to gain an indication of SCC is to conduct what is known as the Californian mastitis test (CMT). This involves mixing a reagent (usually detergent based) with milk. If the milk has a high number of somatic cells (indicating a mastitic condition), then the milk/reagent mixture turns into a thickened jellified fluid. The properties of this fluid result from the strands of DNA from the somatic cells lysed by the reagent, tangling or coagulating. While sufficient mixing can provide an effective flow characteristic which indicates somatic cell count, too much mixing can cause the strands to break, thereby effectively thinning the fluid.

Thus, the fluid properties are difficult to define. It is not thixotropic as the cutting of the strands through over mixing means that the fluid does not return to a gel upon standing. Further, because the fluid is a mixture of DNA strands and other fluid, the fluid is not fully homogenous and is difficult to assign a viscosity reading.

Therefore, it can be appreciated that a solution to the aforementioned problems of not being able to have controlled mixing or measuring is desired.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

DISCLOSURE OF INVENTION

According to another aspect of the present invention, there is provided an instrument for use with fluid which includes
 a mixing element, and
 a container to hold the fluid to be mixed,
 characterised in that
 the mixing element includes a device that assists to measure a parameter of the fluid.

The instrument for use with fluid may be any apparatus which is used to mix a substance to a homogenous or near homogenous state.

The fluid may be any materials which are required to be placed into a homogenous state. For example, the substance may be fluid, powders, or a liquid and a powder or crystal mix. Preferably, the fluid to be mixed are two liquids such as a fluid mixture of milk and a California Mastitis Test (CMT) reagent. This shall be referred to as such throughout the remainder of this specification.

However, persons skilled in the art will appreciate that the present invention has applications across a wide range of industries, for example, food and drink preparation, chemical preparation, and the manufacture of paper. The components of the present invention merely need to be scaled up or down in size as required.

The mixing element may be any element which is to be inserted into the fluid being mixed. For example, the mixing element may be a resonant bar, paddle, or a blade. In one embodiment, the mixing element is a broad, flat element or strap and shall be referred to as a strap when described in this specification.

Later on in this patent specification an alternate form of mixing element would be discussed which is essentially a shuttle.

Preferably, the strap hangs substantially in a vertical orientation into the contents of the container and is secured at our near to the strap's top edge. However, persons skilled in the art will appreciate that the orientation of the strap may vary according to the requirements of the user and the container with which it is to be used. For example, the strap may rest substantially horizontally in the container.

The strap may be constructed from any resilient material such as plastic or metal. Preferably, the strap is manufactured from silicone rubber. Silicone rubber is the preferred material of fabrication as it is flexible, of food grade quality, easy to mould and manufacture and assemble as well as being chemically inert. This latter property prevents the paddle from contaminating the fluid being mixed and analysed.

The strap may include a weight along positioned along at least a portion of its length. Preferably, the weight is positioned substantially at the base or free end of the strap.

Preferably the weight is a dense metal with magnetic or ferromagnetic properties, although persons skilled in the art will appreciate that other materials may be used. In preferred embodiments of the present invention, the weight is a magnet.

The strap may be used with a container with at least an inlet or outlet. In some embodiments of the present invention, the container may have both an inlet and outlet. In some embodiments of the present invention, the inlet may simply be the open top of the container.

The container may be any container suitably configured to hold fluids, powder, or granular material. For example, the container may be a flask or a beaker. Preferably the container is a cell used in a milking machine for the purposes of analysing milk samples. To detect mastitis in cattle, an analysis of milk derived from a cow is tested. The presence of a high number of somatic cells indicates a cow suffering from mastitis. It is common for milking machines to incorporate a cell which contains a milk sample to be analysed for its somatic cell content.

However, persons skilled in the art will appreciate that the strap may be used with other containers depending on the industry in which the user is working.

In one embodiment of the present invention, the strap is fastened to the inside of the container at its upper edge via a clip. In some embodiments of the present invention, the clip of the strap is integrally formed with the strap, while in other embodiments of the present invention, the clip is attached to the strap via fastening means such as a screw or bolt although persons skilled in the art will appreciate that other methods of securing the clip to the strap are envisaged.

The use of a clip allows the strap to be installed and removed as required in between uses. However, some embodiments of the strap may be provided with an aperture for a screw or bolt which can be threaded through the strap and through a corresponding aperture in the container.

In preferred embodiments, one end of the strap is fitted to the inside of a cap to be placed onto an open end of a cell in which the fluid(s) is to be mixed.

In preferred embodiments of the present invention, the strap is secured by one end to the container. The opposing end, which carries the magnet, is unrestrained.

Preferably, the strap does not come into contact with the side of the container and the mounting point of the strap acts as a fulcrum about which the strap moves.

In preferred embodiments of the present invention, an electromagnetic coil is secured nearby or onto the exterior of the container, such that its magnetic field when activated can cooperate with the magnet of the strap. The electromagnetic coil may be secured to the container using adhesive or bolts, although persons skilled in the art will appreciate that other fastening means are envisaged.

In some embodiments of the present invention the container may be configured with a housing for the coil to facilitate easy removal of the coil if required. This will facilitate cleaning of the container as required.

Preferably, the electromagnetic coil is driven at a frequency of 1.25 Hz. The inventor has found that this frequency allows the strap to reach its maximum displacement from its resting position and achieves the fastest apparent mixing of fluids.

However, persons skilled in the art will appreciate that the frequency of the coil may change according to the requirements of the user. For example, if time for ensuring homogeneity of a fluid is a constraint for the user, the frequency of the coil may be higher to ensure the fluid is sufficiently mixed in the appropriate time frame.

When in use, the electromagnetic field generated by the coil can cause the magnet to be forced away from the coil due to the repelling force of the electromagnetic field on the magnet. When the current to the coil is switched off the strap returns via gravity to its resting state, completing a cycle of travel.

Return of the strap from its maximum displacement to its resting position is also aided by the resilience of the silicone rubber from which the strap is constructed.

This process is repeated as required until the fluid which the strap is mixing has met the homogeneity requirements of the user.

Alternatively, the coil can be positioned and operated so it attracts the magnet upwards and then lets the strap fall under gravity when turned off.

This method of mixing fluids minimizes the number of components required for mixing fluids. There are no moving parts which require lubrication or make noise.

Additionally, as only the strap itself makes contact with the fluid being mixed, it is the only component which requires cleaning.

In some embodiments of the present invention, the strap may seal against an inlet or outlet port either at rest or when the strap has been displaced from its resting state.

In preferred embodiments, the fluid parameter being measured is viscosity or an indicator thereof.

It should be appreciated that fluids with such unusual properties as the milk/CMT reagent mixture that the term viscosity may not be a true parameter and what is being measured is some other flow characteristic. Alternate parameters which could be measured include density and salinity.

In preferred embodiments of the present invention, the instrument measures the 'viscosity' of gels formed from the mixing of milk with a reagent for the purposes of determining a somatic cell count (SCC) for a particular milk sample.

In preferred embodiments of the present invention, the electromagnetic coil includes a sensing element to detect changes in the magnetic field of the coil.

When the coil is in a driving mode, the magnetic force causes the magnet attached to the strap to move away from the coil. This causes a signal output due to the change in the electromagnetic field of the coil when the magnet moves to and from its position of rest. A further signal output is caused when the coil's driving mode is deactivated, allowing the strap to return to its stationary position, completing a cycle of travel.

After mixing, the coil is driven for an extended period of time to ensure that the strap is consistently reaching its maximum displacement. The coil is switched off, and the time required for the strap to return to a known point along its path of travel from its maximum displacement is measured. Persons skilled in the art will appreciate that the known point is preferably the point when the strap is at rest, although other reference points may be selected according to the requirements of the user.

With the time required for the strap to return to a known point along its path of travel from its maximum displacement, a measure of viscosity can be determined. A strap moving through a fluid of a high viscosity would take longer to complete a cycle of travel than a strap moving through a fluid of relatively low viscosity.

In preferred embodiments of the present invention, these signals are amplified and filtered before being timed by an electronic circuit (CPU) and visualized on an oscilloscope.

However, persons skilled in the art will appreciate that other methods of cleaning up the transmitted signal, and visualizing the signal may be employed.

In another embodiment of the present invention, the viscometer may include a light emitting device.

Preferably, the light is of an infra-red wavelength, as to prevent ambient light affecting the light beam. However, persons skilled in the art will appreciate that other wavelengths of light may be used depending on the conditions in which the present invention is to be used.

In one mode of operation, from its resting state, the strap moves through the fluid when stimulated by the magnetic field generated from the electromagnetic field. In doing so, the strap breaks the beam of light.

This triggers a time recording device. When the strap returns to its resting state, or another predetermined point along its path of travel, from its extended state, the time recording mechanism is stopped. From the time period recorded from resting state to resting state, a measure of fluid viscosity can be determined.

In some embodiments of the present invention, the strap may consist of a blade, wire or similar structure with minimal surface area.

A reduction in surface area means that the effect of the strap passing through the fluid is minimal in terms of mixing action. In this embodiment of the invention, the strap does not act primarily as a mixer. Instead, the primary function of the strap is more as a fluid sensor.

An alternate form of the present invention which uses a number of the principles applied to the strap has an unattached pod or shuttle as the mixing element.

In preferred embodiments of the present invention the shuttle contains a magnet, or a ferromagnetic material.

The requirements for the shuttle are similar to that of the strap. It needs to travel well within the container, be easily cleaned and therefore have smooth lines with minimal crevasses.

It is envisaged that the preferred emotion of the shuttle will be substantially up and down within a narrow container or tube with the driving means for this motion being substantially the same as for the strap, that is the action of gravity and/or magnetic.

To work well, the shuttle will need to fall uniformly.

It is envisaged that in some embodiments there will be provided guides on the body of the shuttle to ensure that it maintains in a substantially upright orientation with regard to the container in which it is used. In some embodiments these guides may be in the form of fins, although it is envisaged that other types of guides may be used.

In embodiments which utilise fins, it should be appreciated that various configurations can be used. For example, there could be any number of fins although it is envisaged that there will be in the order of 3 to 4. In some embodiments, the fins will be substantially straight being aligned with the sides of the container into which the shuttle is to be placed.

An alternate embodiment, the fins may have a helical turn which could cause rifling of the shuttle as it descends in the container thereby helping maintain its upright orientation.

Fins are preferred as the use of these could enable the shuttle to be made with the low cross-sectional area with regard to the path of its travel. This provides flow pathways for the fluid within the container to flow around the shuttle. This is in direct contrast to most viscometers which have flow problems due to a large ball used within a small area.

Further considerations as to the physical configuration of the shuttle would be to include perhaps having the shuttle bottom weighted. This lower centre of gravity provides greater stability for the shuttle when falling through the container. In some embodiments, the bottom weight may be the actual magnet or magnetic material itself.

Another consideration is that the lower the fall time of the shuttle within the container (or rise time) the greater the resolution there can be in determining the parameter associated with the time of the drop or fall (e.g. viscosity). Therefore, some embodiments of the present invention may have the shuttle being made from a low density material (apart from maybe the sensor itself) or even a part which provides resistance to flow such as a flared top of the device.

In some embodiments, the shuttle may merely be an appropriately shaped ferromagnetic material without a body carrying it.

In one embodiment of the present invention there may be provided a magnetic device which drags the shuttle up through the fluid and then can be turned off to enable the shuttle to drop down. The time that the shuttle takes to go downwards is indicative of the property of the fluid in which the shuttle has been placed.

Alternatively, there may be provided a magnet near the base of the container which repels the shuttle upwards. That same magnet (preferably in the form of an electromagnetic coil) could also act as a sensor that notes the fall time with the shuttle.

In one in preferred embodiments, the fall time is a time from when the magnet releases the shuttle to when it passes another sensor. In some embodiments the "fall time" could be the time taken from when the shuttle is driven upwards and falls down without a holding period in between.

If a coil is used to drive up the shuttle, then the positioning of the coil and the relative to the container and the shuttle is very important, Ideally the centre of the coil is slightly below the centre of the magnetic material within the shuttle when the shuttle is at rest at the bottom of the container. If not, then the coil would not be able to drive the shuttle upwards.

As can be seen, one of the principles of the present invention is to be able to mix and sense with the same device. With the shuttle embodiment a typical sequence by which the present shuttle can be used to give an indication of somatic cell count in milk is as follows.

First, a predetermined amount of milk and reagent is introduced into the container. This amount may be determined through the use of various sampling methods.

For example the user may merely pour the required volume of milk and reagent into the container.

Alternatively, there may be provided some automatic means whereby a level sensor can detect once a certain volume of reagent has been introduced. Various means may be used to sense the level of fluid. For example, optical methods may be used, conductivity probes, capacitive sensors and the like. Combinations of various level sensors may also be used.

At this stage, the shuttle and magnet is resting at the base of the container.

A coil around the base of the container is then turned on and the resultant electromagnetic field repels the magnet in the shuttle, causing the shuttle to rise towards the top of the container.

The coil is then turned on and off in a sequence causing the shuttle to move back and forth. Approximately 5 strokes in approximately 1.5 seconds works particularly well. The inventors have found that this is sufficient agitation to mix the milk and reagent together without over mixing and possible breakage of coagulating DNA strands.

The fluid in the container is then allowed to rest for approximately 10 to 30 seconds so the milk and reagent have time to react and gel.

Following that the shuttle is again propelled towards the top of the container and held there. The shuttle may be held with a stop against which it pushed by the electromagnetic field from the coil, or in some embodiments by a further coil at the top of the container.

Next the shuttle is released from the top and allowed to fall downwards through the jellified liquid under the force of gravity. The effect of the moving magnet within the shuttle on the magnetic field of the coil is detected. Once the shuttle reached the bottom of the container (and therefore is not moving) zero voltage is detected. Thus, the time between when the shuttle has started its fall and stopped can be readily measured irrespective of actual amplitude of the signal received as a consequence.

It has been found that the fall time versus the actual somatic cell count can fit a calibration curve enabling SCC to be relatively easily calculated.

The present invention provides apparatus and a method of using the apparatus for mixing and analysing of fluids. It offers a number of advantages over the prior art:

- The present invention is quiet due to not requiring an electrically driven motor unit, and thus is relatively inaudible. This makes its use in a laboratory setting or another environment where little noise is preferred ideal.
- It has relatively few moving parts. Because of this, the present invention requires no lubrication agents which can potentially contaminate the fluid being mixed. This makes the present invention ideal for use in mixing and analysing fluids for particularly sensitive tests which can be easily contaminated.
- It can be easily adapted to varying sized containers. The strap or shuttle can be unclipped or unfastened, cleaned, and used in another container as required.
- The strap itself, not having any surface blemishes or textural configurations is easily cleaned. Being made from chemically inert silicone is also advantageous when being used for particularly sensitive scientific tests prone to contamination.
- The strap or shuttle has a path of travel which does not inhibit the inlet or outlet ports of scientific glassware or whatever container is being used for analysis of fluids. This allows the use of the present invention in containers with ports that potentially could be blocked if a traditional magnetic stirrer or measurement instruments were used
- The present invention can determine a measure of the viscosity of the fluid while being mixed. This eliminates the need to stop mixing the fluid in order to gain a measure of viscosity.
- The present invention is easily integrated into the cells of milking machines for the purposes of assessing the somatic cell in a milk sample.
- The present invention can also determines the viscosity of a fluid much more quickly and accurately than with traditional viscosity measurement instruments.
- The present invention allow measurement of fluid viscosity using means which does not inhibit the inlet or outlet ports of whatever container is being used, unlike traditional viscosity measurement apparatus such as Falling Sphere Viscometers which measure the rate of vertical descent through a container of a sphere.
- Integrating the viscometer with the mixing element also reduces the number of components required for measuring viscosity.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

Figure 1:
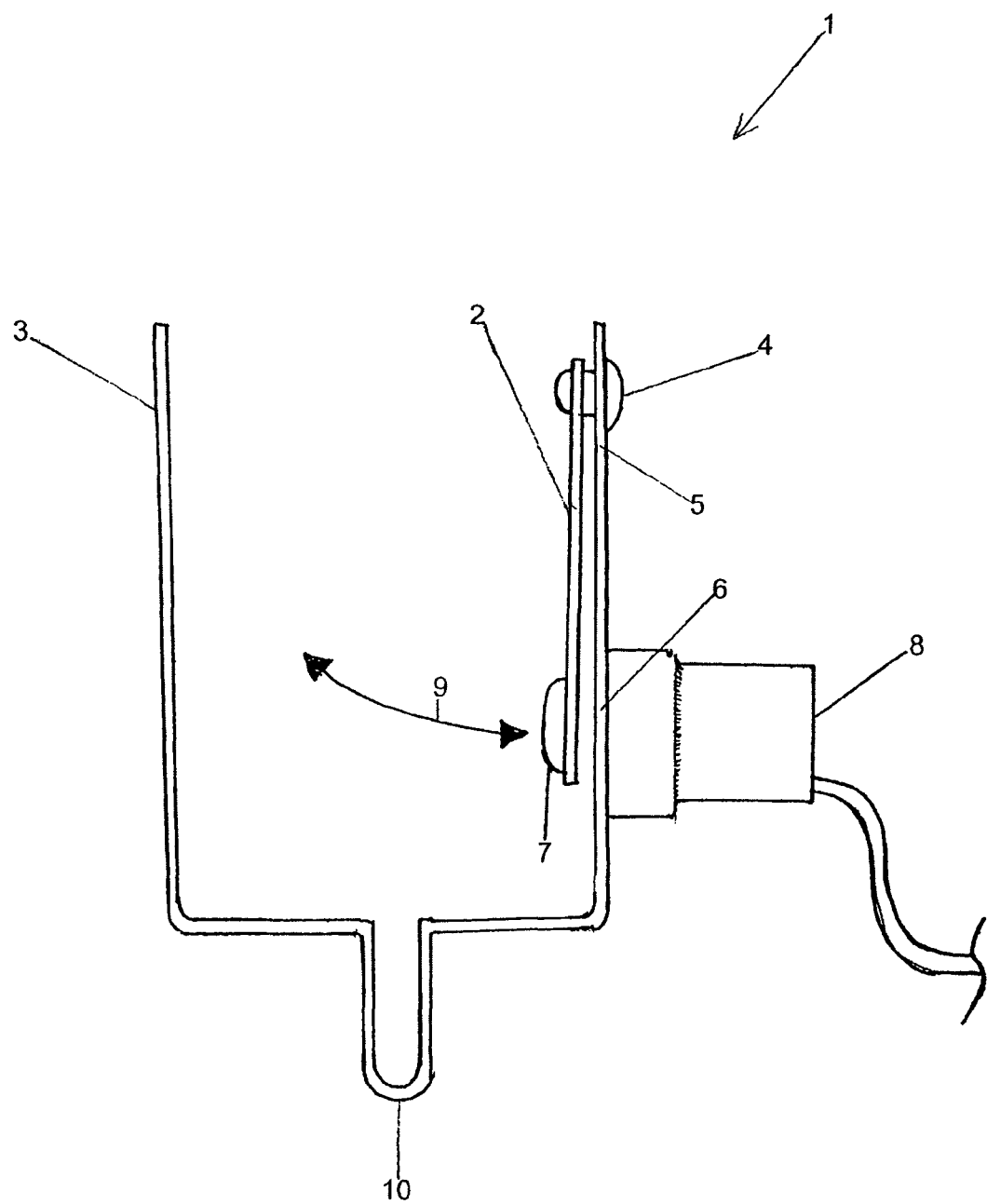
FIG. 1 is a side view of one embodiment of the present invention.

FIG. 1 illustrates the present invention (indicated generally by arrow 1), which includes the strap (2) mounted to the interior of a sample cell (3) via a fastener (4).

A spacer (5) ensures that the body of the strap (2) is kept from making contact with the side wall of the container (6). This spacer (5) also acts as a fulcrum for the motion of the strap (2).

At the tip of the strap (2) there is provided a magnet (7). On the exterior side of the cell (3) closest to the magnet (7) is an electromagnetic coil (8). The face (not shown) of the electromagnetic coil (8) is secured to the side wall of the cell (6) by adhesive.

In use, the electromagnetic coil generates a magnetic field, causing the strap to move in the path of travel indicated by arrow 9, as it is repelled by the electromagnetic coil (8). It should be appreciated that this path of travel does not inhibit the inlet/outlet (10) of the cell, permitting passage of additional fluids if required.

Figure 2:
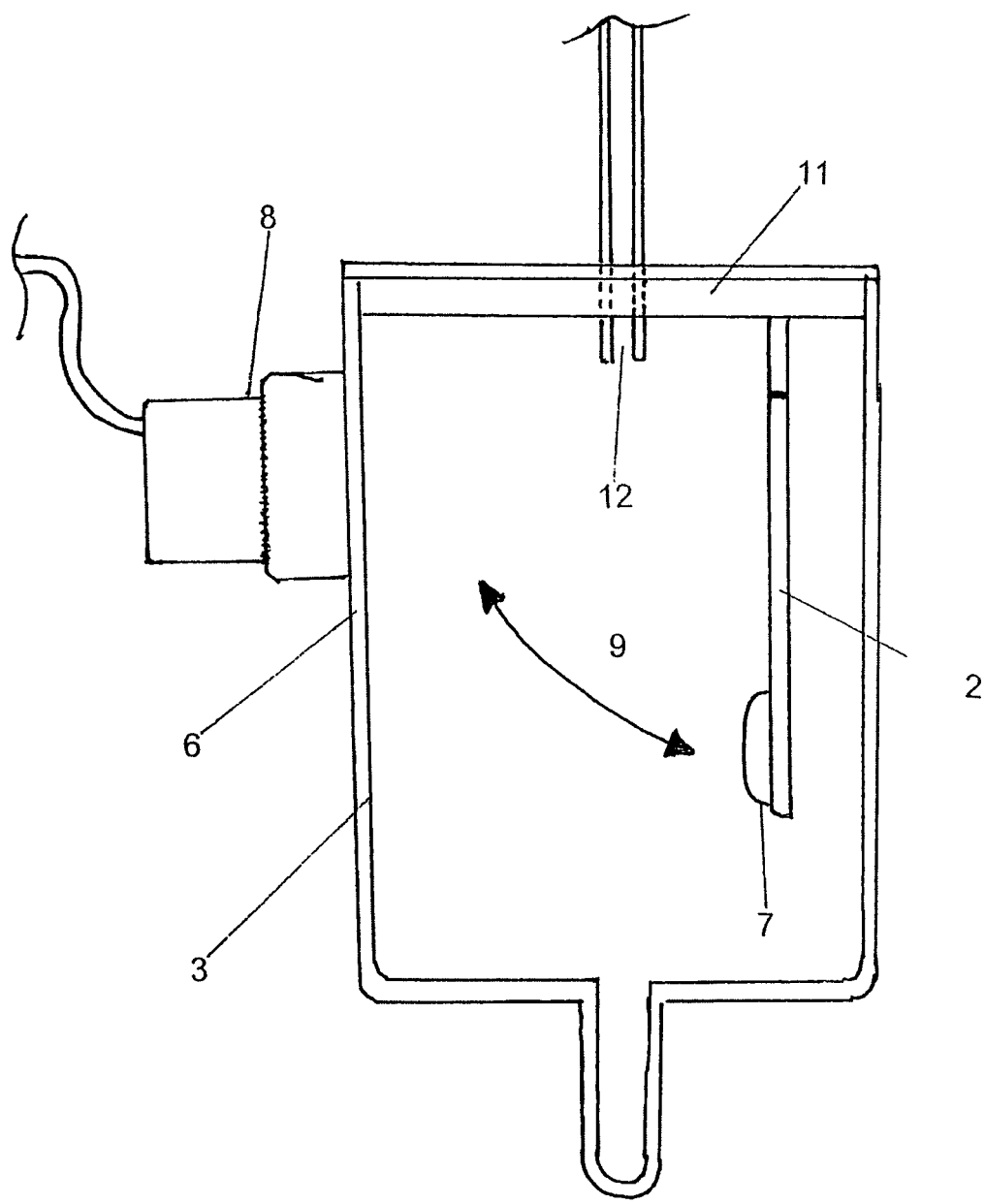
FIG. 2 is a side view of another embodiment of the present invention.

Another embodiment of the present invention is illustrated in FIG. 2.

The strap (2) is secured to a lid (11) for the cell (3) containing fluid to be analyzed.

The lid (11) is provided with an inlet (12) for fluid to pass into the cell (3).

The side wall of the cell (6) carries an electromagnetic coil (8). In contrast to the electromagnetic coil illustrated in FIG. 1, in this embodiment of the present invention the electromagnetic coil (8) is place on the opposite cell wall (6) to the strap (2).

In use, activation of the electromagnetic coil (8) causes an attraction force on the magnet (7) of the strap. This forces the strap (2) to move in the path of travel indicated by arrow 13.

Cessation of the electromagnetic force allows gravity to act upon the Strap (2), returning it to its rest position.

It will be appreciated that this path of travel (13) does not inhibit the inlet (11) or outlet (12) of the cell, permitting passage of additional fluids if required.

Figure 3:
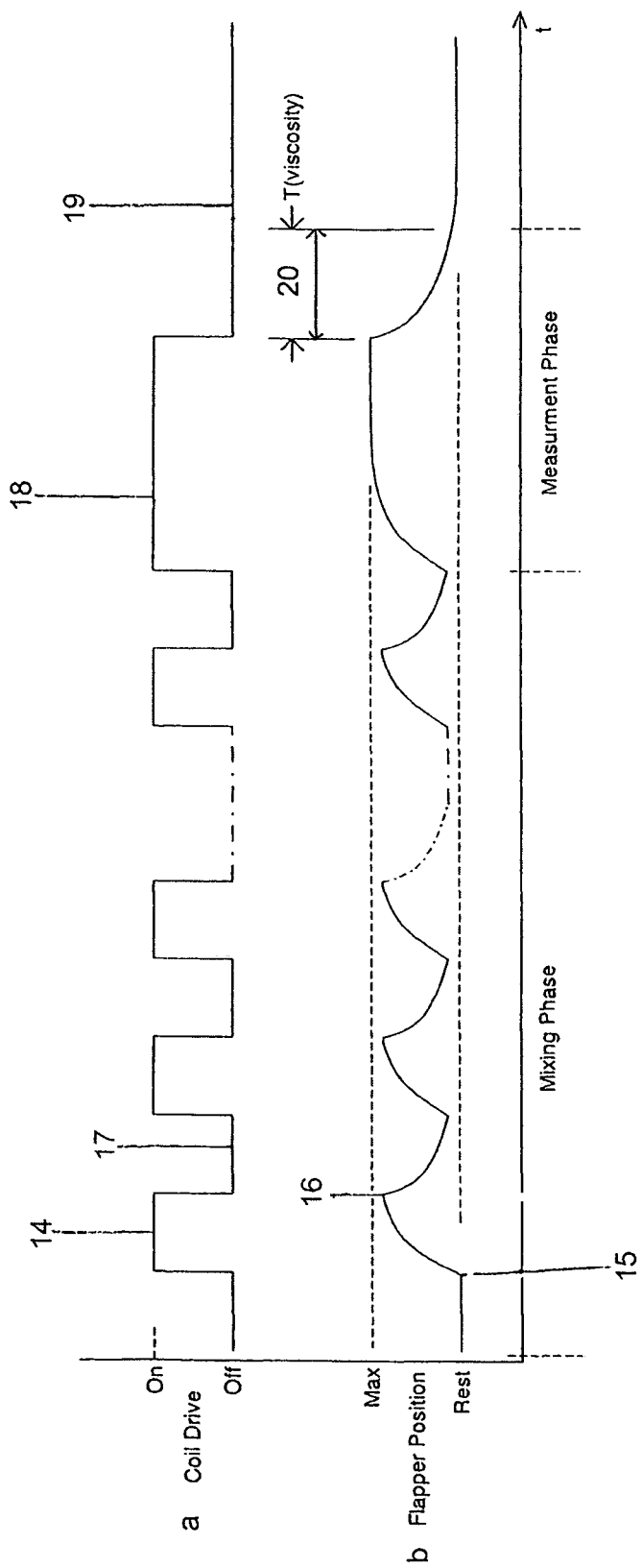
FIG. 3 is a graphical representation of the coil drive and its relationship to the position of the strap of the present invention.

FIG. 3 illustrates graphically the relationship between the electromagnetic coil (a) and the position of the strap (b).

When the coil drive is activated (14) it causes displacement of the strap from its rest position (15) to its maximum displacement (16), as the magnet interacts with the electromagnetic field generated by the coil drive.

When the coil drive is deactivated (17), the strap returns its rest position. This can be repeated as required to create a mixing motion as the strap moves through the fluid being mixed.

When being used as a viscometer, the coil drive is activated for an extended period of time (18) to ensure that the strap has reached its maximum displacement. When the coil drive is deactivated (19), the time taken (20) for the strap to return to its position of rest is measured and is a measure of viscosity.

Figure 4:
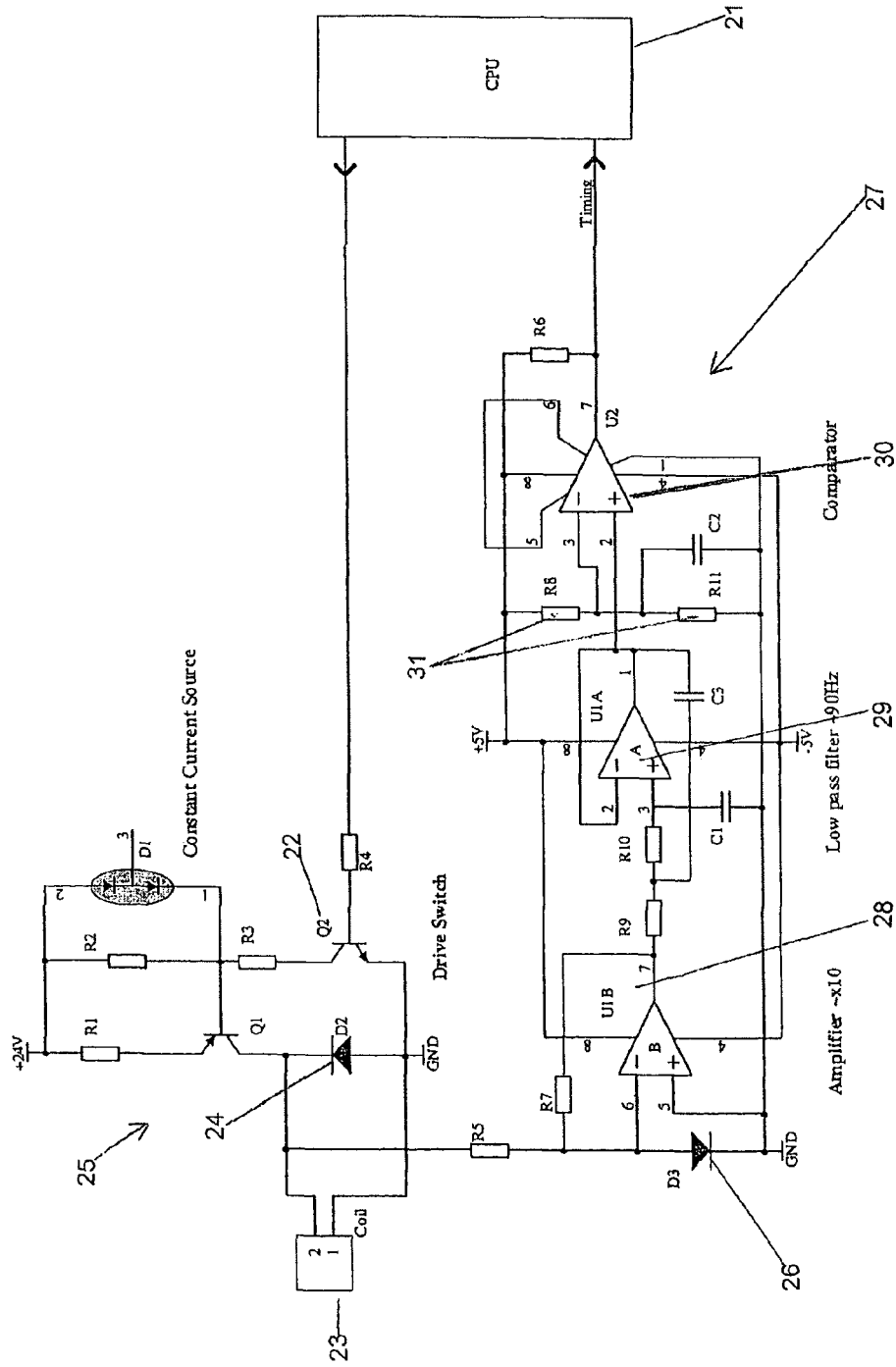
FIG. 4 is a schematic for operation of the strap of the present invention, and FIG. 5a,b,c,d illustrates alternate configurations of a shuttle in accordance with one embodiment of the present invention.

FIG. 4 illustrates a schematic for operation of the present invention.

Control of the overall strap circuit is via a central processing unit (CPU) (21).

The CPU (21) turns the Coil Drive Switch (22) on and off to activate and deactivate the coil (23).

This activation of the coil drive causes an electromagnetic field, displacing the magnet secured to the tip of the strap from its position of rest. The change in the electromagnetic field as the magnet moves through the field is recorded (not shown).

A voltage clamp (24) is provided to protect the strap drive circuit (generally indicated by arrow 25) from short high voltages which may be induced in the coil (23).

A further voltage clamp (26) is provided in the strap timing circuit (generally indicated by arrow 27).

When a signal is received from the strap coil (23), it is passed through an amplifier (28). The signal emitted by the coil as the magnet falls back to its rest position following release can be very small, and requires amplification for further processing of the signal.

However, amplification of the signal also can result in an increase in the noise of the signal, and therefore the strap timing circuit (27) also includes a low pass filter (29) which removes most of the noise from the signal.

A comparator (30) is employed to convert the analog coil signal into a digital signal which can be timed by the CPU (21). This allows for higher resolution timing of the signal. With the presently used CPU, an analog signal can be recording to the nearest 50μ second, while a digital signal can time to the nearest 0.5μ second.

Voltage dividers (31) are used to set the detection point of the signal when the strap is returning to its position of rest.

FIG. 5 illustrates various configurations of its shuttle which can be used in accordance with the present invention.

FIG. 5a illustrates a shuttle generally indicated by arrow (50) which includes a central body (51) with four fins (52) extending outwardly therefrom. The central body (51) has an aperture (53) along the length thereof. The aperture (53) is of a size and shape that it can receive a magnet (54) therein.

The shuttle (55) in FIG. 5b is essentially the same shuttle as illustrated in FIG. 5a with the exception that the top of the shuttle (55) includes a flared portion (56) which adds drag to the shuttle (55) as descends through the fluid within the container.

The shuttle (57) illustrated in FIG. 5c is again very similar to that in FIG. 5a, the main difference is that it has only three fins (58).

Figure 5D:
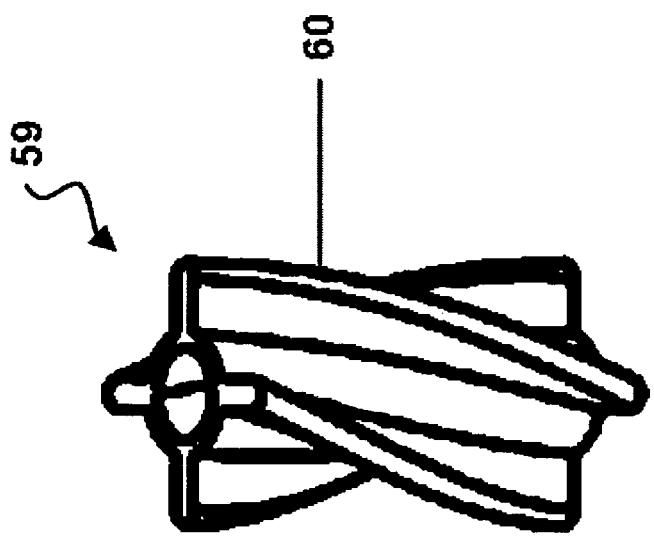

The shuttle (59) in FIG. 5d has four fins as in the shuttle (50) but these are in a helical configuration.

Figure 6:
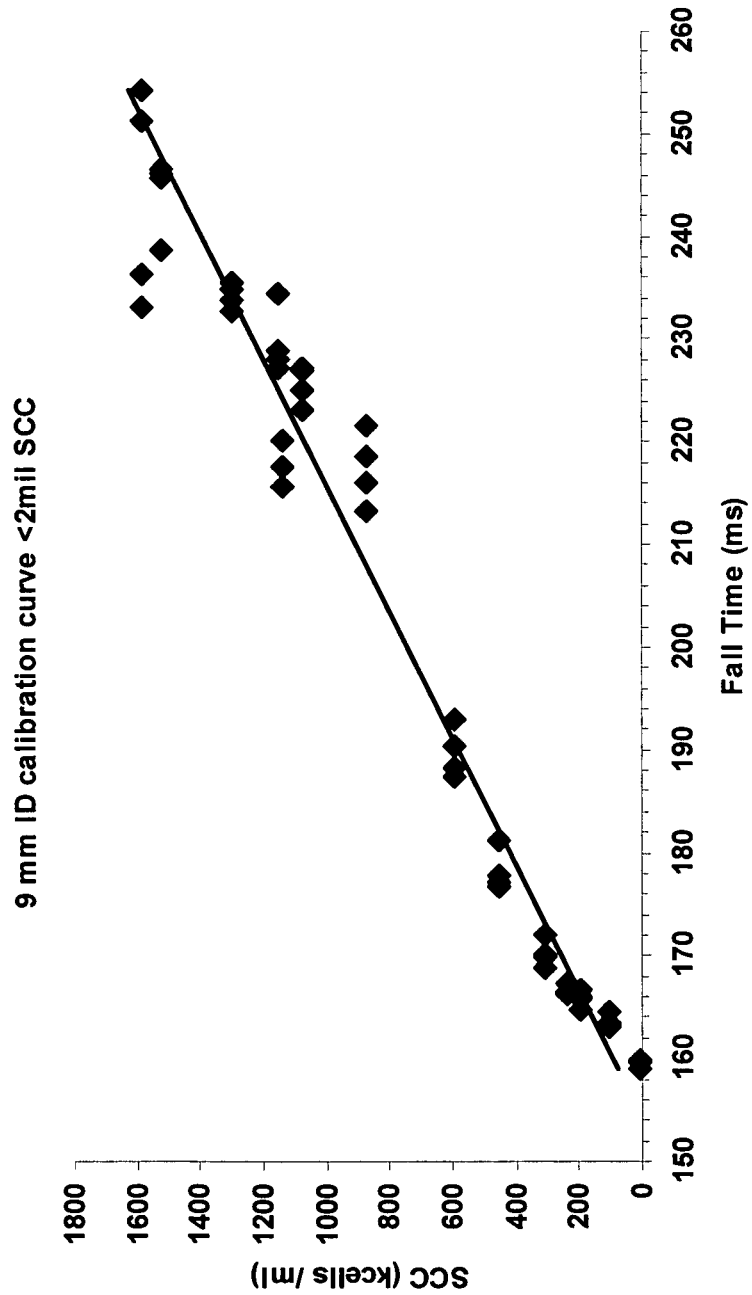
FIG. 6 illustrates a comparison of fall times with SCC.

FIG. 6 illustrates typical fall times of the shuttle as illustrated in FIG. 5a compared against measured somatic cell count. As can be seen, the repeated results are highly consistent and fit a calibration curve.

Figure 5C:
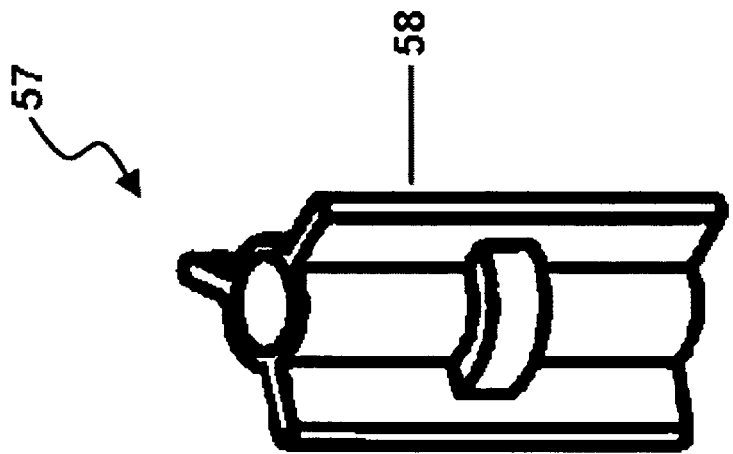
Figure 7:
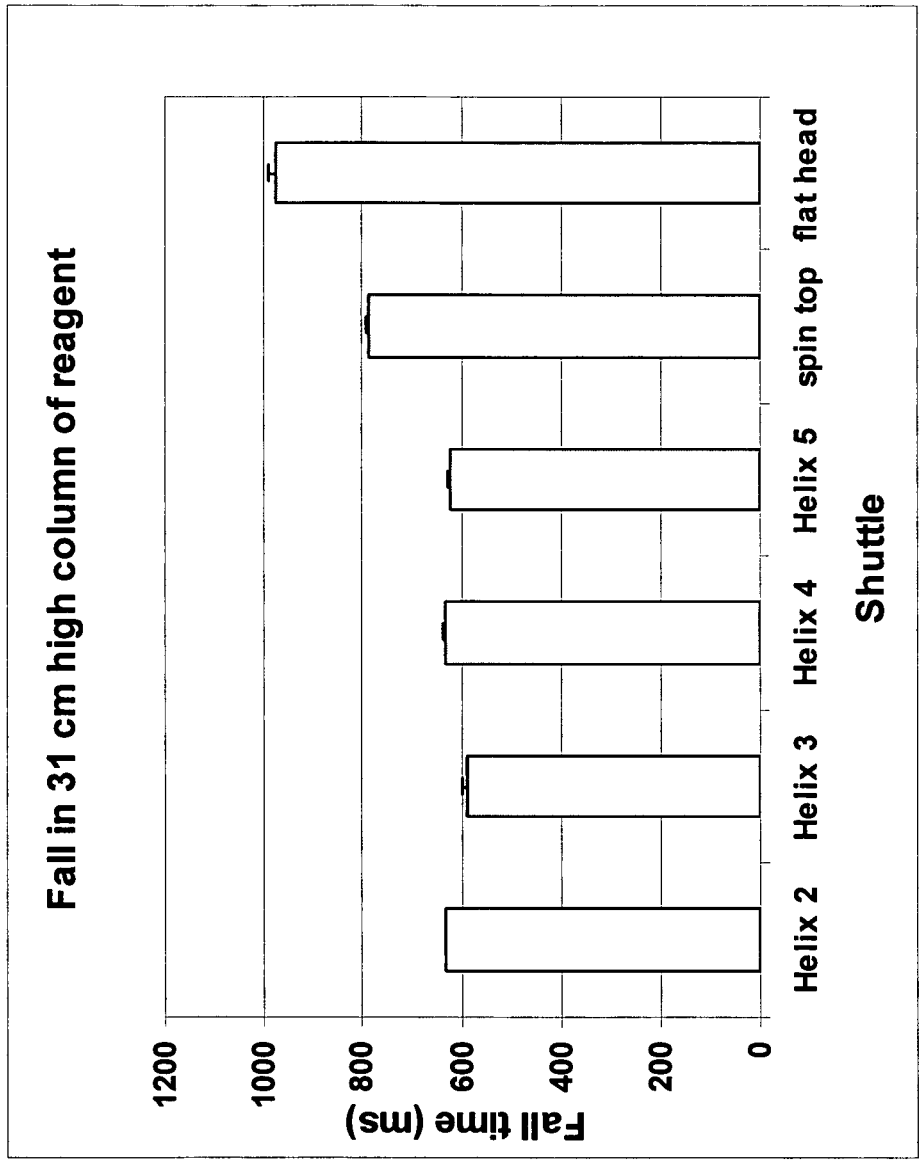
FIG. 7 illustrates fall times with different shuttle configurations.

FIG. 7 illustrates different fall times of shuttles having different shapes in a reagent having the same viscosity. The fall time of the shuttle through the reagent is influenced by its shape. The flat head shuttle (56) is shown in FIG. 5B. The spin top shuttle (58) is shown in FIG. 5C. The Helix shuttle (60) is shown in FIG. 5D. Four Helix shuttles were tested, each with a different amount of twist. Overall the flat head shuttle had the longest fall time, and therefore gave the greatest resolution.

Figure 8:
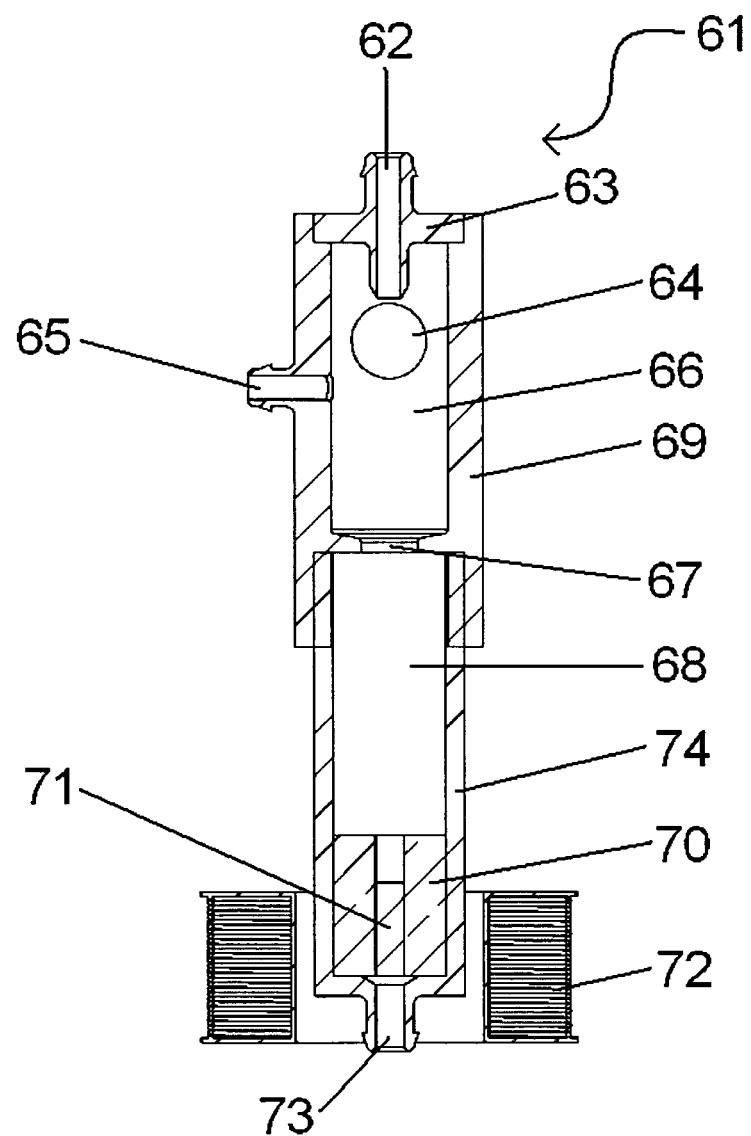
FIG. 8 is a cross-sectional view of an instrument in accordance with one embodiment of the present invention.

FIG. 8 is a cross sectional view of an instrument generally indicated by arrow (61) constructed with accordance with one embodiment of the present invention.

At the top of the instrument (61) is a milk inlet (62) which is in the form of a conduit passing through a milk inlet cap (63).

At the upper side of the instrument (61) is an overflow port (64).

At right angles to the overflow (64) is a reagent inlet (65).

It can be seen that when either the milk or the reagent is introduced into an upper chamber (66), they pass under the influence of gravity through an inlet orifice (67) into a lower chamber (68).

The total volume of milk and reagent added to the instrument should be such that the fluid level is above the top of the inlet orifice (67), in order to avoid air bubbles and non-homogeneous mixing.

The inlet orifice (67) acts as a physical stop for the travel of the shuttle. When the coil is activated the shuttle is held against the stop, giving a defined path of travel when the coil is then deactivated and the shuttle drops under gravity.

The lower chamber (68) is in essence formed by the lower chamber body (74). The lower chamber (68) contains the shuttle (70).

In this view of the present invention, the shuttle (70) is sitting at the base of the instrument (61). Within the shuttle (70) is the shuttle magnet (71).

Surrounding the base of the instrument (61) is a coil (72) which acts both as a driver for the magnet (71) and a fluid sensor.

Below the shuttle (70) in the base of the instrument (61) is a waste outlet (73).

It can be seen that the shuttle (70) is constrained in its movement within the lower chamber (68) as a consequence of
 a) close tolerances between the shuttles outer edges and the internal diameter of the lower shuttle body (74), and
 b) the inlet orifice (67) preventing the shuttle from entering the upper chamber (66).

The positioning of the magnet (71) within the shuttle (70) is such that activation of the coil (72) can only cause the magnet (71) (and hence the shuttle (70)) to travel upwards within the lower chamber (68). Deactivation of the coil (72) causes the shuttle (70) to drop downwards under gravity.

The speed of the descent of the shuttle under gravity is measured by the induced signal in the coil (72), and is related to fluid viscosity.

Aspects of the present invention have been described by way of example only and it should be appreciated that modifications and additions may be made thereto without departing from the scope of the appended claims.

What I claim is:

1. An instrument in a milking machine for measuring viscosity of gels formed from mixing milk with a reagent in order to determine a somatic cell count for a particular milk sample, comprising:
 a mixing element, wherein the mixing element is a shuttle and contains a magnet or ferromagnetic material which assists in measuring a viscosity by a fall time of the mixing element in the milk and reagent to be mixed;
 a container to hold the milk to be mixed, the container including a chamber for the mixing element;
 a driving means for the mixing element positioned exterior to an inner surface of the container and the mixing element and the milk with the reagent to be mixed;
 wherein the driving means is not physically connected to the mixing element, and the mixing element is not attached to the container;
 wherein the driving means is an electromagnetic coil which drags the shuttle up through the milk and can be turned off to enable the shuttle to drop down, or which is provided near the base of the container and repels the shuttle upwards, and which is configured to sense changes in the magnetic field;
 wherein the shuttle includes guides in the form of fins that are substantially straight and aligned with the sides of the container into which the shuttle is to be placed,
 and wherein the chamber includes an inlet for the milk and an inlet for the reagent, and wherein at least one inlet opens into the chamber from the upper side of the instrument.

2. The instrument as claimed in claim 1 wherein the driving means is positioned on an exterior surface of the container.

* * * * *